US006383630B1

(12) United States Patent
Jauchen et al.

(10) Patent No.: US 6,383,630 B1
(45) Date of Patent: May 7, 2002

(54) AIR-PERMEABLE SUBSTRATE MATERIAL PARTIALLY COATED WITH A SELF-ADHESIVE SUBSTANCE, PROCESS FOR ITS PRODUCTION AND ITS USE

(75) Inventors: Peter Jauchen, Hamburg; Peter Himmelsbach, Buxtehude, both of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/171,175

(22) PCT Filed: Apr. 26, 1997

(86) PCT No.: PCT/EP97/02178

§ 371 Date: Oct. 14, 1998

§ 102(e) Date: Oct. 14, 1998

(87) PCT Pub. No.: WO97/43993

PCT Pub. Date: Nov. 27, 1997

(30) Foreign Application Priority Data

May 18, 1996 (EP) .......................... 196 20 107

(51) Int. Cl.[7] .............................. A61F 13/02; C09J 7/02
(52) U.S. Cl. ................................ 428/343; 428/355 AL; 428/355 AC; 428/346; 442/150; 427/208.2; 427/208.4
(58) Field of Search .................... 428/355 BL, 343, 428/346, 356, 355 AC; 442/150; 427/208.2, 208.4

(56) References Cited

U.S. PATENT DOCUMENTS

| 4,139,613 A | * | 2/1979 | Hefele .................... 427/197 |
| 4,818,610 A | * | 4/1989 | Zimmerman et al. ....... 428/345 |
| 5,342,858 A | * | 8/1994 | Litchholt et al. .......... 521/98 |
| 5,389,168 A | * | 2/1995 | Litchholt et al. .......... 156/77 |
| 5,605,717 A | * | 2/1997 | Simmons et al. ........ 427/208.2 |

FOREIGN PATENT DOCUMENTS

| DE | 3741194 A1 | * | 12/1987 |
| FR | 2 318 914 | * | 6/1976 |

* cited by examiner

Primary Examiner—Daniel Zirker
(74) Attorney, Agent, or Firm—Norris McLaughlin & Marcus

(57) ABSTRACT

Carrier material having a self-adhesive finish and a hotmelt self-adhesive composition applied not to the entire area of at least one side, characterized in that the adhesive composition is foamed.

12 Claims, No Drawings

AIR-PERMEABLE SUBSTRATE MATERIAL PARTIALLY COATED WITH A SELF-ADHESIVE SUBSTANCE, PROCESS FOR ITS PRODUCTION AND ITS USE

The invention relates to carrier materials which have been treated to make them self-adhesive and which are coated over not the entire area of at least one side with a hotmelt self-adhesive composition, to a process for their preparation and to their use.

Hotmelt self-adhesive compositions based on natural and synthetic rubbers and other synthetic polymers are known and are increasingly being employed. Their essential advantage is that, unlike compositions which are applied from solution or as an aqueous dispersion, there is no need for the laborious and in some cases environmentally polluting techniques of removing the solvents or the water.

It is also known to apply such self-adhesive compositions not only over the entire area but also in the form of a pattern of dots, for example by screen printing (DE-C 42 37 252), in which case the dots of adhesive can also differ in their size and/or distribution (EP-B 353 972), or by intaglio printing, in lines which interconnect in the longitudinal and transverse directions (DE-C 43 08 649).

The advantage of the patterned application is that the adhesive materials, given an appropriately porous carrier material, are permeable to air and water vapour and in general are readily redetachable.

A disadvantage of these products, however, is that if the area covered by the adhesive film, which per se is impermeable, is too large there is a corresponding reduction in the permeability to air and water vapour, and the consumption of adhesive composition rises, and, if the area covered by the adhesive film is small, the adhesion properties suffer, i.e. the product is detached too readily from the substrate.

The object of the invention, therefore, was to avoid these disadvantages and to develop a product and process featuring—given an appropriately porous carrier material—very good permeability to air and water vapour and also generally good adhesion properties coupled with low consumption of adhesive composition.

This object is achieved by a carrier material which has been given a self-adhesive finish and has a hotmelt adhesive composition applied not over the entire area of at least one side, which material is characterized in that the adhesive composition is foamed.

This foamed self-adhesive layer applied not over the entire area can be patterned, preferably in dome form by means of screen printing, or else can be applied in a different pattern, such as lattices, stripes, zigzag lines and, for example, also by intaglio printing. Furthermore, it can, for example, also be sprayed on, giving a more or less irregular application pattern.

The self-adhesive composition can be distributed uniformly on the carrier material; however, it can also be applied with varying thickness or density as appropriate for the function of the product.

Depending on the carrier material and its sensitivity to temperature, the self-adhesive layer can be applied directly or first applied to an auxiliary carrier and then transferred to the final carrier. In addition, subsequent calendering of the coated product and/or pretreatment of the carrier, such as corona treatment, for better anchoring of the adhesive layer may be advantageous.

The percentage of the area coated with foamed self-adhesive composition should be at least 20% and can range up to about 95%, for specific products preferably 40–60%. and from 70 to 95%. The weight per unit area of the applied adhesive composition should be at least 15 g/m² in order to give sufficient adhesion levels, preferably 30–160 g/m² depending on the carrier employed.

The adhesive compositions are preferably foamed using inert gases such as nitrogen, carbon dioxide, noble gases, hydrocarbons or air, or mixtures thereof. In some cases, foaming by thermal decomposition of gas-evolving substances such as azo, carbonate and hydrazide compounds may also prove suitable.

The degree of foaming, i.e. the proportion of gas, should be at least about 10% by volume and can range up to about 80%. Values which have been found favourable in practice for the proportion of gas are 30–70%, preferably 50%. Operation at relatively high temperatures of around 100° C. and at a comparatively high internal pressure produces open-pored adhesive foam layers which are of particularly good permeability to air and water vapour. The dot pattern of the coating supports the air permeability values within broad limits.

If no particular worth is attached to this property, it is also possible, by altering the parameters, to produce and use closed-pored foam structures.

Self-adhesive compositions which can be employed are the known thermoplastic hotmelt adhesive compositions based on natural and synthetic rubbers and on other synthetic polymers such as acrylates, methacrylates, polyurethanes, polyolefins, polyvinyl derivatives, polyesters or silicones with appropriate additives such as adhesion resins, plasticizers, stabilizers and other auxiliaries where necessary. Their softening point should be higher than 80° C., since the application temperature is generally at least 90° C., preferably between 120 and 150° C. or 180–220° C. in the case of silicones. If desired, postcrosslinking by UV or electron-beam irradiation may be appropriate.

Self-adhesive compositions which have proven particularly suitable are those based on A-B-A block copolymers which consist of hard and soft segments. A is preferably a polymer block based on styrene and B is preferably a polymer block based on ethylene, propylene, butylene, butadiene, isoprene or mixtures thereof such as ethylene-butylene. In addition, hotmelt adhesive compositions of this kind generally comprise one or more aliphatic or aromatic hydrocarbon resins as adhesion resins, one or more medium- or long-chain fatty acids or esters thereof, and also stabilizers and, if desired, other auxiliaries. The ranges for the amounts of the constituents are generally between 15–70% block copolymers, 20–70% adhesion resins, 10–50% plasticizers and small amounts of stabilizers and other auxiliaries.

Carrier materials which can be employed are virtually all carriers which are commonly used for industrial or medical purposes, i.e. woven or knitted materials, elastic or inelastic materials, plastics films or metal foils, papers, nonwovens, foam materials or laminates thereof.

The carrier materials which have been given a self-adhesive treatment and which, in accordance with the invention, are partially coated with a foamed hotmelt self-adhesive composition are notable for a range of advantages. As a result of the foaming of the adhesive composition and the consequent pores in the composition, when the carrier used is porous per se the regions coated with adhesive composition are also of good permeability to water vapour and air. The amount of adhesive composition required is considerably reduced with no adverse effect on the adhesive properties. The adhesive compositions are of surprisingly high tack, since per gram of composition there is more volume and thus adhesive surface area for the wetting of the substrate on which bonding is to take place, and the plasticity of the adhesive compositions is increased as as result of the foam structure. In addition, anchorage on the carrier material is thereby improved. Furthermore, the foamed adhesive coating gives the products a soft and smooth feel.

The subjective advantages of the product, tack and smoothness, can readily be quantified using a dynamomechanical frequency measurement. In this case, use is made of a rheometer controlled by shearing stress.

The results of this measurement method give information on the physical properties of a substance by taking into account the viscoelastic component. In this instance, at a preset constant temperature, the hotmelt pressure-sensitive adhesive is set in oscillation between two plane-parallel plates with variable frequencies and low deformation (region of linear viscoelasticity). Via a pickup control unit, with computer assistance, the quotient (Q=tan δ) between the loss modulus (G", viscous component) and the storage modulus (G', elastic component) is determined. A high frequency is chosen for the subjective sensing of the tack and a low frequency for the smoothness, and the corresponding quotients are determined via the degree of foaming. The higher the corresponding numerical value of the quotient, the better the subjective property.

The tack and the smoothness were improved in accordance with the invention, as shown in the table.

$$Q = \tan \delta = G''/G'$$

| Designation | Smoothness low frequency/RT | Tack high frequency/RT |
| --- | --- | --- |
| Pressure-sensitive hotmelt adhesive A (unfoamed) | tan δ = 0.35 ± 0.05 | tan δ = 0.45 ± 0.05 |
| Pressure-sensitive hotmelt adhesive A Foam vol. ($N_2$) = 50% | tan δ = 0.46 ± 0.05 | tan δ = 0.65 ± 0.05 |
| Pressure-sensitive hotmelt adhesive A (unfoamed) | tan δ = 0.35 ± 0.05 | tan δ = 0.45 ± 0.05 |
| Pressure-sensitive hotmelt adhesive A Foam vol. ($N_2$) = 70% | tan δ = 0.58 ± 0.05 | tan δ = 0.88 ± 0.05 |
| Pressure-sensitive hotmelt adhesive B (unfoamed) | tan δ = 0.05 ± 0.03 | tan δ = 0.84 ± 0.05 |
| Pressure-sensitive hotmelt adhesive B Foam vol. ($N_2$) = 50% | tan δ = 0.27 ± 0.05 | tan δ = 1.15 ± 0.05 |
| Pressure-sensitive hotmelt adhesive C (unfoamed) | tan δ = 0.06 ± 0.03 | tan δ = 0.93 ± 0.05 |
| Pressure-sensitive hotmelt adhesive C Foam vol. ($N_2$) = 50% | tan δ = 0.31 ± 0.05 | tan δ = 1.25 ± 0.05 |

Different pressure-sensitive hotmelt adhesives were chosen, i.e. A based on acrylate and B and C on block copolymers, and the results indicate a marked rise in the tan δ values as a result of foaming, i.e. a measurably better smoothness and tack.

The advantages demonstrated make the novel carrier materials particularly suitable for medical purposes. Plasters or bandages, or dressings that are additionally provided with a wound pad, are, given an appropriately chosen air-permeable carrier material and a hypoallergenic adhesive composition, of especially good skin compatibility, since they are of pronounced permeability to air and water vapour over the entire area and are soft and smooth. They have a cushioned effect and as a result couple good properties when being worn with good adhesion.

In addition, cohesive adhesion coatings, i.e. anti-slip coatings, which stick only to themselves or have a virtually non-adhering character, can be produced in accordance with the invention.

Where specially shaped plasters are to be produced, the coating of adhesive composition can be printed on in direct correspondence with the product, by means of appropriate stencils, and then the plasters can be punched out in sharp definition.

The advantageous properties of the novel adhesive coatings, such as low consumption of adhesive, high tack and good smoothness on both regular and uneven surfaces, owing to the elasticity and plasticity of the foamed adhesive compositions, can also be utilized in a pure industrial field. The resulting self-adhesive tapes and other products given a self-adhesive finish in this way are versatile in their possibilities for use.

A particularly suitable process for producing the carrier materials which are, in accordance with the invention, given a self-adhesive finish operates in accordance with the foam-mix system. In this process, the thermoplastic pressure-sensitive adhesive is reacted under high pressure at about 120 degrees Celsius with dry gases, such as nitrogen, air or carbon dioxide, in different proportions by volume (about 10–80%) in a stator/rotor system. Whereas the gas feed pressure is >100 bar, the mixing pressures of gas/thermoplastic in the system are 40–100 bar, preferably 40–70 bar. The pressure-sensitive adhesive foam produced in this way passes through a line into the supply nozzle of a meltscreen printing coating unit.

The principle of thermal rotary screen printing consists in the use of a rotating, heated, seamless, drum-shaped, perforated, cylindrical stencil which is fed via a nozzle with the foamed pressure-sensitive adhesive composition. A specially shaped nozzle lip (circular or square doctor blade) presses the self-adhesive composition in foam form, which is fed in via a channel, through the perforation of the stencil wall and onto the carrier web that is conveyed past it. This carrier web is guided by means of a counterpressure roller against the external jacket of the heated screen drum at a rate which corresponds to the peripheral speed of the rotating screen drum.

In this context, the formation of the small domes of adhesive foam takes place by the following mechanism:

The pressure of the nozzle doctor blade conveys the foam adhesive composition through the screen perforation onto the carrier material. The size of the domes formed is determined by the diameter of the screen perforation. The screen is lifted from the carrier in accordance with the rate of transportation of the carrier web (rotary speed of the screen drum). As a consequence of the high adhesion of the foam adhesive composition and the inner cohesion of the hotmelt, the limited supply of foam adhesive composition in the perforations is drawn off in sharp definition from the base of the domes that is already adhering to the carrier, and is conveyed by the blade pressure onto the carrier.

After the end of this transportation of foam, the more or less highly curved surface of the foam dome forms over the predefined base area in dependence on the rheology of the foam adhesive composition. The ratio of height to base of the dome depends on the ratio of the perforation diameter to the wall thickness of the screen drum and on the physical properties (flow behaviour, surface tension and wetting angle on the carrier material) of the foam adhesive composition.

The described mechanism of formation of the foam domes requires carrier materials which are absorbent or at least wettable by foam adhesive compositions. Non-wetting carrier surfaces must be pretreated by chemical or physical methods. This can be effected by means of additional measures such as corona discharge, for example, or by coating with substances which improve wetting.

Using the pressure technique indicated it is possible to lay down the size and shape of the foam domes in a defined manner. The adhesive force values which are relevant for use and which determine the quality of the products formed are within very narrow tolerances in the case of proper coating. The base diameter of the domes can be chosen from 10–2000 $\mu$m, the height of the domes from 20—about 2000 $\mu$m, preferably 50–1000 $\mu$m, the low-diameter range being intended for smooth carriers and the range of greater diameter and greater dome height being intended for rough or highly porous carrier materials.

The positioning of the foam domes on the carrier is laid down in a defined manner by the geometry of the applicator unit, for example the engraving or screen geometry, which can be varied within wide limits. With the aid of the parameters indicated it is possible, by way of adjustable variables, to establish with very great precision the desired profile of properties of the coating, harmonized with the various carrier materials and uses.

It has additionally been found that any carrier, if appropriate after pretreatment, can be printed regardless of the surface roughness and absorbency, and in a very economic manner.

Using the printing technique of coating it is possible to carry out direct coating of many carriers provided that they are of sufficient thermal stability. However, it is universally employable for all flat and three-dimensional carriers as well through the so-called transfer process, in which the adhesive layer is first applied to an intermediate carrier and then transferred to the ultimate carrier.

The invention is illustrated in more detail below by means of examples:

EXAMPLE 1

The preparation was carried out in accordance with the invention of an ophthalmic occlusion plaster which is employed for the prophylaxis and therapy of strabismus and of amblyopia in children. This plaster consists of an elastic woven cotton structure which has been coated by thermal screen printing with an adhesive composition based on a block copolymer.

The block copolymer is a styrene-ethylene-butylene-styrene block copolymer to which paraffinic hydrocarbons have been added. The ratio is in this case two parts of polymer to one part of paraffinic hydrocarbons. The adhesive contains 1% anti-ageing agent (n-octadecycl $\beta$-(3,5-di-t-b utyl-4-hydroxyphenyl)-propionate, trade name: IRGANOX 1076) and other hydrocarbon resins and fatty acid esters which are present only in small amounts in the overall adhesive. The adhesive is obtainable commercially (from Fuller). The adhesive composition was foamed with nitrogen in a ratio of 1:2 at 120° C. by the method described. The resulting proportion of gas in the end product is 50%. On the adhesive layer of 30 g/m$^2$ there was fastened, centrally, a multilayer insert consisting of a cover film, light protection insert, absorbent film and an additional lattice film for covering, leaving a sufficient adhesive edge exposed. The complete plaster was encased with a siliconized release paper.

The adhesive composition was applied to the carrier by screen printing in such a way that there was more adhesive composition at the edges than in the centre of the plaster. The coating dots on the edge of the plaster were chosen to be as large as possible in order to ensure the adhesion of the adhesive composition on the carrier and to ensure high security of adhesion. In the centre of the plaster, the chosen application of adhesive composition was just enough to ensure that the insert is fastened securely on the carrier. It was possible to make a saving on further adhesive composition as a result of the sharply defined printing. This is possible by way of the selection of the screen stencil. After coating, the plaster was punched out accordingly. The adhesive layer which comes into contact with the skin is of pronounced permeability to air and water vapour, and the tack is very good. Owing to the high cohesion of the adhesive and the associated, relatively low epilation of the eyebrow, the plaster can be pulled off again readily and almost painlessly.

EXAMPLE 2

To date, elastic bandages have generally been coated indirectly. In such coating, the adhesive composition is spread out onto silicone-coated release paper and the solvent is removed in a drying tunnel. The elastic carrier material, a woven or knitted structure, is then laminated on. However, a bandage produced in this way is not always of sufficient air-permeability.

A bandage produced in accordance with the invention was coated by thermal screen printing with an application of about 160 g/m$^2$ of an adhesive composition based on a block copolymer. The block copolymer is a styrene-ethylene-butylene-styrene block copolymer to which paraffinic hydrocarbons have been added. The ratio in this case is one part of polymer to one part of paraffinic hydrocarbon. 10% of polystyrene resin (e.g. Amoco 18240) were added to the mixture produced. The adhesive also contains one percent of anti-ageing agent (n-octadecyl $\beta$-(3,5-di-t-butyl-4-hydroxyphenyl)-propionate, trade name IRGANOX 1076) and other hydrocarbon resins and fatty acid esters, which are present only in small amounts in the overall adhesive. The adhesive is obtainable commercially (from Fuller). The adhesive composition was foamed with nitrogen in a ratio 1:2 at 120° C. by the method described above. The resulting proportion of gas in the end product was then 50%.

The high level of application of the composition was achieved using a 14 mesh screen stencil with 50% passage. For the use of large coating dots it was possible to obtain good adhesion on the carrier and clean cutting. As a result of the foamed, open-pored adhesive composition, the bandage is permeable to air and water vapour even in a multilayered dressing. It is employed for compression, support and relief dressings, in which contexts the high immediate and long-term adhesive strength are advantageous. Furthermore, the adhesive composition based on the block copolymer supports, through the elasticity of the adhesive, the compressive action of the bandage. The modelling properties and user perception are improved by the foaming of the adhesive composition.

EXAMPLE 3

This example illustrates the use of the invention for dressings. In this case, a film of polyurethane having a thickness of 60 $\mu$m is coated by thermal screen printing with a foamed acrylate hotmelt adhesive composition. The adhesive composition is applied directly to the film in accordance with the punched contour. The amount of adhesive applied is 60 g/m$^2$ in the edge zone and 25 g/m$^2$ in the central zone.

After coating, the central zone is covered with a wound pad, preferably consisting of a nonwoven or foam having a superabsorbing action. The plaster is subsequently processed further in a customary manner and, if desired, is sterilized by means of γ radiation. Over its entire area the dressing is respiration-active and permeable to water vapour, as a result of which the skin is protected against macerations and the dressing can be worn for longer. In addition, as a result of the high amount of adhesive composition applied in the external edge zones, reliable adhesion has been achieved.

EXAMPLE 4

This example shows the use of the invention for a fingertip dressing. In this case, a nylon nonwoven with a thickness of 60 μm is coated by thermal screen printing with a foamed styrene-ethylene-butylene-styrene block copolymer hotmelt adhesive composition. The adhesive composition is applied directly to the nonwoven in accordance with the punched contour. The amount of adhesive applied is 60 g/m² in the edge zone and 25 g/m² in the central zone. After coating, the central zone is provided with a wound pad, preferably consisting of a nonwoven or foam having a superabsorbing action, and the plaster, after encasement with the customary protective covering, is punched out and packaged.

What is claimed is:

1. Carrier material having a self-adhesive finish comprising a hotmelt self-adhesive composition applied not to the entire area of at least one side, wherein the adhesive composition is foamed.

2. Carrier material having a self-adhesive finish according to claim 1, wherein the foamed adhesive composition is applied in a pattern by screen printing or intaglio printing.

3. Carrier material having a self-adhesive finish according to claim 1, wherein the foamed adhesive composition is sprayed on.

4. Carrier material having a self-adhesive finish according to claim 1, wherein the adhesive composition is applied over the surface in varying thicknesses and/or densities as appropriate for the function of the product.

5. Carrier material having a self-adhesive finish according to claim 1, wherein the adhesive composition is applied with a surface coverage of 20–95%.

6. Carrier material having a self-adhesive finish according to claim 1, wherein the adhesive composition is foamed with an inert gas selected from the group consisting of nitrogen, carbon dioxide, noble gases, hydrocarbons, air, and mixtures thereof.

7. Carrier material having a self-adhesive finish according to claim 1, wherein the proportion of gas in the adhesive composition is 10–80 percent by volume.

8. Carrier material having a self-adhesive finish according to claim 1, wherein the adhesive composition is composed on an A-B-A block copolymer basis, A being polystyrene and B being selected from the group consisting of ethylene, propylene, butylene, butadiene, isoprene and mixtures thereof.

9. Process for producing carrier material having the self-adhesive finish of claim 1, wherein the hotmelt self-adhesive compositions are reacted under high pressure with inert gases in proportions by volume of 10–80% in a stator/rotor system, to produce a pressure-sensitive adhesive foam which is then passed into the supply nozzle of a melt-screen printing rotary coating device, and is applied thereby to the carrier material.

10. Process according to claim 9, wherein the adhesive composition is applied in the form of small domes to the carrier material.

11. Medical products comprising a carrier material having a self-adhesive finish according to claim 1.

12. Medical products according to claim 1, wherein said medical products are members of the group consisting of sticking plasters, fixing plasters, test plasters, rapid dressings, bandages, orthopedic bandages, wound pads, incision films and colostomy bags.

* * * * *